United States Patent [19]

Ertinghausen

[11] Patent Number: 5,087,556
[45] Date of Patent: Feb. 11, 1992

[54] METHOD FOR QUANTITATIVE ANALYSIS OF BODY FLUID CONSTITUENTS

[75] Inventor: Gerhard Ertinghausen, Princeton, N.J.

[73] Assignee: Actimed Laboratories, Inc., Mount Laurel, N.J.

[21] Appl. No.: 352,985

[22] Filed: May 17, 1989

[51] Int. Cl.$^5$ .................. G01N 33/543; G01N 33/558
[52] U.S. Cl. ...................................... 435/7.9; 436/514; 436/518; 436/807; 435/291; 435/810; 435/975; 422/56; 422/57; 422/58; 422/61
[58] Field of Search ............ 435/7.9, 808, 291; 436/514, 807, 518; 422/56

[56] References Cited

U.S. PATENT DOCUMENTS

| | | | |
|---|---|---|---|
| 3,552,925 | 1/1971 | Fetter | 435/805 |
| 3,791,933 | 2/1974 | Moyer et al. | 435/28 |
| 3,802,842 | 4/1974 | Lange et al. | 436/169 |
| 3,964,871 | 6/1976 | Hochstrasser | 23/253 |
| 3,983,005 | 9/1976 | Goodhue et al. | 195/103.5 |
| 4,042,329 | 8/1977 | Hochstrasser | 23/230 |
| 4,186,251 | 1/1980 | Tarbutton | 435/11 |
| 4,233,029 | 11/1980 | Columbus | 422/58 |
| 4,298,688 | 11/1981 | Kallies | 435/14 |
| 4,435,504 | 3/1984 | Zuk et al. | 495/7 |
| 4,477,575 | 10/1984 | Vogel et al. | 436/170 |
| 4,594,327 | 6/1986 | Zuk | 436/514 |
| 4,608,336 | 8/1986 | Benovic et al. | 435/805 |
| 4,632,901 | 12/1986 | Valkirs et al. | 436/807 |
| 4,637,978 | 1/1987 | Dappen | 435/28 |
| 4,678,757 | 7/1987 | Rapkin et al. | 422/56 |
| 4,680,259 | 7/1987 | Cumbo et al. | 435/28 |
| 4,756,884 | 7/1988 | Hillman et al. | 422/73 |
| 4,761,381 | 8/1988 | Blatt et al. | 436/165 |
| 4,774,192 | 9/1988 | Terminiello et al. | 436/810 |
| 4,973,549 | 11/1990 | Khanna et al. | 422/56 |

FOREIGN PATENT DOCUMENTS

| | | |
|---|---|---|
| 0317070 | 5/1989 | European Pat. Off. |
| 0330517 | 8/1989 | European Pat. Off. |
| 0342447 | 11/1989 | European Pat. Off. |

OTHER PUBLICATIONS

Sloan et al., "The Quantab Strip in the Measurement of Urinary Chloride and Sodium Concentrations" *Clin. Chem.* 30 (10), 1705–1707, (1984).

*Primary Examiner*—Sam Rosen
*Assistant Examiner*—Christopher L. Chin
*Attorney, Agent, or Firm*—Iver P. Cooper

[57] ABSTRACT

The invention is a self-contained, chromatic quantitative analyzer that quantitatively detects an analyte in a biological fluid. The invention includes a base having a first open reservoir for receiving the biological fluid. A means for separating solids from the biological fluid is provided in the first open reservoir. A channel is provided which draws, by capillary and/or wicking action, the biological fluid from the first open reservoir to a second open reservoir. The second open reservoir draws the biological fluid from the channel and, when the second open reservoir is full with the biological fluid, the capillary and/or wicking action terminates. A membrane is provided in the channel which is permeable to the biological fluid. There is at least one chromatic chemical indicator immobilized in the membrane in a predetermined concentration. The membrane enables the biological fluid to interact with the chromatic chemical indicator.

14 Claims, 2 Drawing Sheets

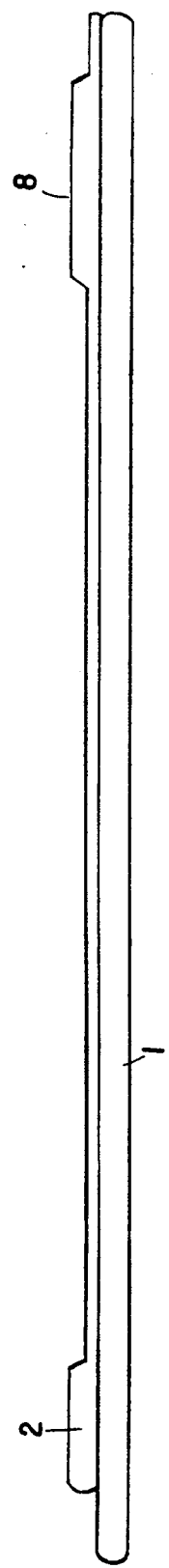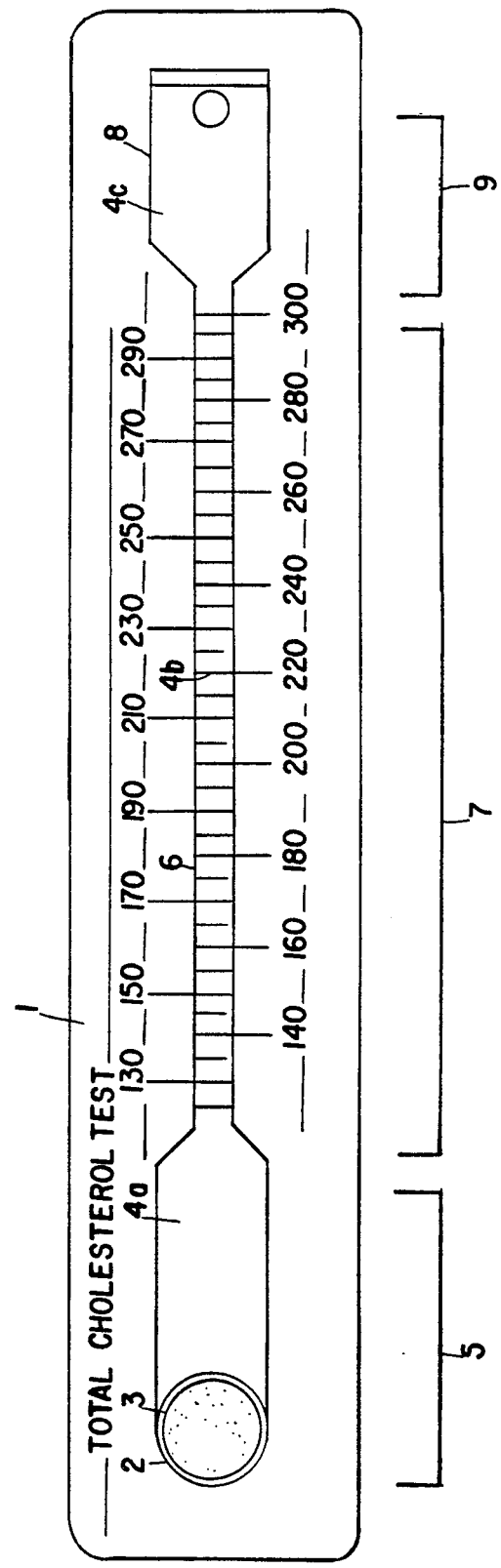

METHOD FOR QUANTITATIVE ANALYSIS OF BODY FLUID CONSTITUENTS

BACKGROUND OF THE INVENTION

1. Field of the Invention

This invention relates to a device and method for quantitative analysis of body fluid constituents. Specifically, this invention relates to a device and a method for quantitatively analyzing constituents of whole blood or other body fluids with self-contained, ready-to-use test strips and the process to manufacture the device.

2. Description of the Background Art

Medical science has an increasing need for quick, accurate determination of analytes in blood or other body fluids. Traditionally, assays for analytes have been performed by laboratories and required skilled technicians, complex apparatus and reagents, and considerable time in order to determine accurate results. Numerous qualitative and some quantitative devices and methods have been developed which eliminate or decrease the need for laboratory diagnostic services. Many of these devices and methods include test strips or dip sticks which can be exposed to blood or another body fluid in order to obtain a diagnostic result. A common example of this technology includes the various test products for determining the concentration of glucose in diabetics.

The determination of the concentration of glucose and other analytes has been performed by various devices and methods using either urine or blood as the body fluid sample. The most common of these tests are dip sticks for testing the concentration of glucose in urine. The dip sticks are dipped into a sample of urine and then undergo a color change. The color of the dip stick is compared to a chart of color references on the label of the container providing the dip stick. When the color of the dip stick is matched to the color reference, one determines the approximate glucose concentration from the color reference. Similar tests exist wherein paper strips are used to determine the concentration of glucose in whole blood. These tests are also conducted by comparing the amount of color formation of the paper strip to a standard. These semi-quantitative tests do not accurately determine the concentration of an analyte in the blood being tested unless an instrument is used.

U.S. Pat. No. 4,435,504 to Zuk, et al., discloses an immunochromatographic assay with support having bound "MIP" or antibody and a second enzyme. This invention measures the amount of analyte in a sample solution of a body fluid by combining a premeasured volume of sample with a premeasured volume of a solution of enzyme labelled analyte and immunochromatographing the solution or employing a combination of enzymes wherein one enzyme is the label and the other enzyme is affixed to the chromatographic support. The assay of this invention is performed by contacting the immunochromatograph with the sample containing solution. The sample traverses a region of the immunochromatograph by elution or solvent transport. The device used in this assay has a region in which the antibody is non-diffusively bound to a bibulous support. The analyte from the sample and its enzyme labelled conjugate traverse this zone along with the solvent. The analyte and its enzyme labelled analogue become bound to the support through the intermediacy of antibody complex formation. The signal producing system provides the area in this region with a color change which identifies the distance from a predetermined point over which the analyte and its enzyme labelled conjugate have traveled. In this manner, a quantitative determination of the analyte can be made. This invention does not directly test whole blood and requires accurate volumetric measurement of the sample and the enzyme conjugate solution and dilution of the sample by a separately applied solvent. Furthermore, the determination of the analyte concentration with this invention requires the use of a separate "signal producing system". The invention of this disclosure does not provide an immediate determination of the concentration of an analyte.

U.S. Pat. No. 4,594,327 to Zuk discloses an assay method for whole blood samples. This invention uses at least one specific binding pair which is substantially, uniformly bound to a solid bibulous element. The method to use this invention requires that the sample be mixed in an aqueous medium with a binding agent. This invention also requires a separate signal producing system such as that discussed for the patent above. The invention of this disclosure does not provide a self-contained unit that accurately determines the quantitative concentration of an analyte without the use of additional solvents or reagents.

An article by Sloan, et al., discloses "The Quantab Strip in the Measurement of Urinary Chloride and Sodium Concentrations" *CLIN. CHEM.* 30 (10), 1705–1707 (1984). The test strip of this disclosure provides a quantitative measurement of chloride and sodium concentrations in urine. The test strips of this disclosure rely on wicking alone and do not provide an additional capillary channel to speed up the process. The porous matrix typically requires between 15 to 30 minutes to draw urine up the entire measurement zone. The device of this article does not provide a rapid quantitative test, a channel or a separation means for solids.

U.S. Pat. Nos. 3,964,871 and 4,042,329 to Hochstrasser disclose a method and device for detecting either glucose or cholesterol. The device of these disclosures is dipped into a sample of body fluid. The fluid reacts with an analyte. The concentration of the analyte correlates with a color intensity scale which translates into an approximate quantitative determination of the analyte. The device of these disclosures does not provide an accurate, sensitive quantitative test for analytes.

U.S. Pat. No. 4,761,381 to Blatt et al. discloses a volume metering capillary gap device for applying a liquid sample onto a reactive surface. The device of this patent controls a liquid volume flowing onto a reactive surface by use of an overflow chamber. The capillary channel leading to the overflow chamber is controlled so that liquid cannot flow back into a reaction chamber. The method of analysis conducted by the Blatt et al. invention introduces liquid very quickly into the device (within 2 seconds) in order to prevent slow entry by simultaneous capillary action in the channel and wicking through the porous matrix at the bottom of the device. The geometry of the detection chamber determines the volume used for the test. Blatt et al. have two compartments connected "in parallel" to the sample entry port, i.e., liquid flowing from the entry port into the overflow chamber does not flow through the reaction chamber. The geometry of their reaction chamber, though rectangular, is not channel or appropriate for a measurement scale. This device can receive blood as a sample fluid, however, this device has no means for separating the cells from the plasma.

U.S. Pat. No. 4,756,884 to Hillman, et al., discloses a capillary flow device. The device provides for measuring a sample, mixing the sample with reagents, defining a flow path, and reading the result. The capillary tube of this device provides the sole driving source for the movement of liquid through the device. The use of this device primarily involves tests requiring blood agglutination and optical readers to determine test results. This device does not provide a self-contained quantitative analysis device for measuring analytes.

U.S Pat. No. 4,477,575 to Vogel et al. discloses a process and composition for separating plasma and serum from whole blood. This invention uses a composition of glass fibers having an average diameter of from $0.2\mu$ to $0.5\mu$ and a density of 0.1 $g/cm^2$ to 0.5 $g/cm^2$. The total volume of the plasma or serum separated from the blood is limited to at most 50% of the absorption volume of the glass fiber layer. Other fibers are disclosed as being useful in forming the composition with the glass fiber. The test devices disclosed in this patent do not meter plasma flow through the device nor provide a quantitative analysis of an analyte.

The industry lacks a device for quantitative analysis of constituents of whole blood or other body fluids that is fast, accurate, and completely self-contained.

SUMMARY OF THE INVENTION

The invention is a self-contained chromatic quantitative analyzer that quantitatively detects an analyte in a biological fluid. The invention includes a base having a first open reservoir for receiving the biological fluid. A means for separating solids or retarding their flow is provided in the first open reservoir. A channel is provided which draws, by capillary action, the biological fluid from the first open reservoir to a second open reservoir. The second open reservoir draws the biological fluid through the channel. When the second open reservoir is full with the biological fluid, the capillary action is terminated. A membrane is provided in the channel and is permeable to the biological fluid, but impermeable to any cells it contains. There is at least one chromatic chemical indicator immobilized in the membrane in a calibrated or predetermined concentration. The membrane enables the biological fluid to interact with the chromatic chemical indicator. The chromatic chemical indicator detects the analyte in the biological fluid by reacting with the analyte, a reaction product of the analyte, or a labelled analogue developing a color. The colored portion of the channel caused by reaction of the chromatic chemical indicator with the analyte, or a derivative thereof, as observed after the capillary action is terminated, corresponds to the concentration of the analyte in the biological fluid. A scale is provided along the channel to readily equate the colored portion of channel to the concentration of analyte.

The invention also includes a method for quantifying an analyte by using the device of this invention. The method involves receiving a biological fluid in a first open reservoir of a base. Separating of any solids suspended in the biological fluid then occurs in the first open reservoir. Drawing of the biological fluid through a channel, by capillary and/or wicking action is then performed from the first open reservoir to a second open reservoir. The second open reservoir contains an absorbent. The second open reservoir draws the biological fluid from the channel and, when the second open reservoir is full with the biological fluid, the capillary and/or wicking action is terminated. While the biological material is being drawn through the channel, a membrane in the channel is permeated with the biological fluid. The membrane has at least one chromatic chemical indicator immobilized in itself in a predetermined concentration to interact with the biological fluid. The method then involves reacting, completely, an analyte in the biological fluid present in the channel, in a single step or a series of chemical reactions, with the chromatic chemical indicator.

BRIEF DESCRIPTION OF THE DRAWINGS

FIG. 1 illustrates a plan view of the device of the invention.

FIG. 2 illustrates a side view of the device of the invention.

DETAILED DESCRIPTION OF THE INVENTION

Figure 3:
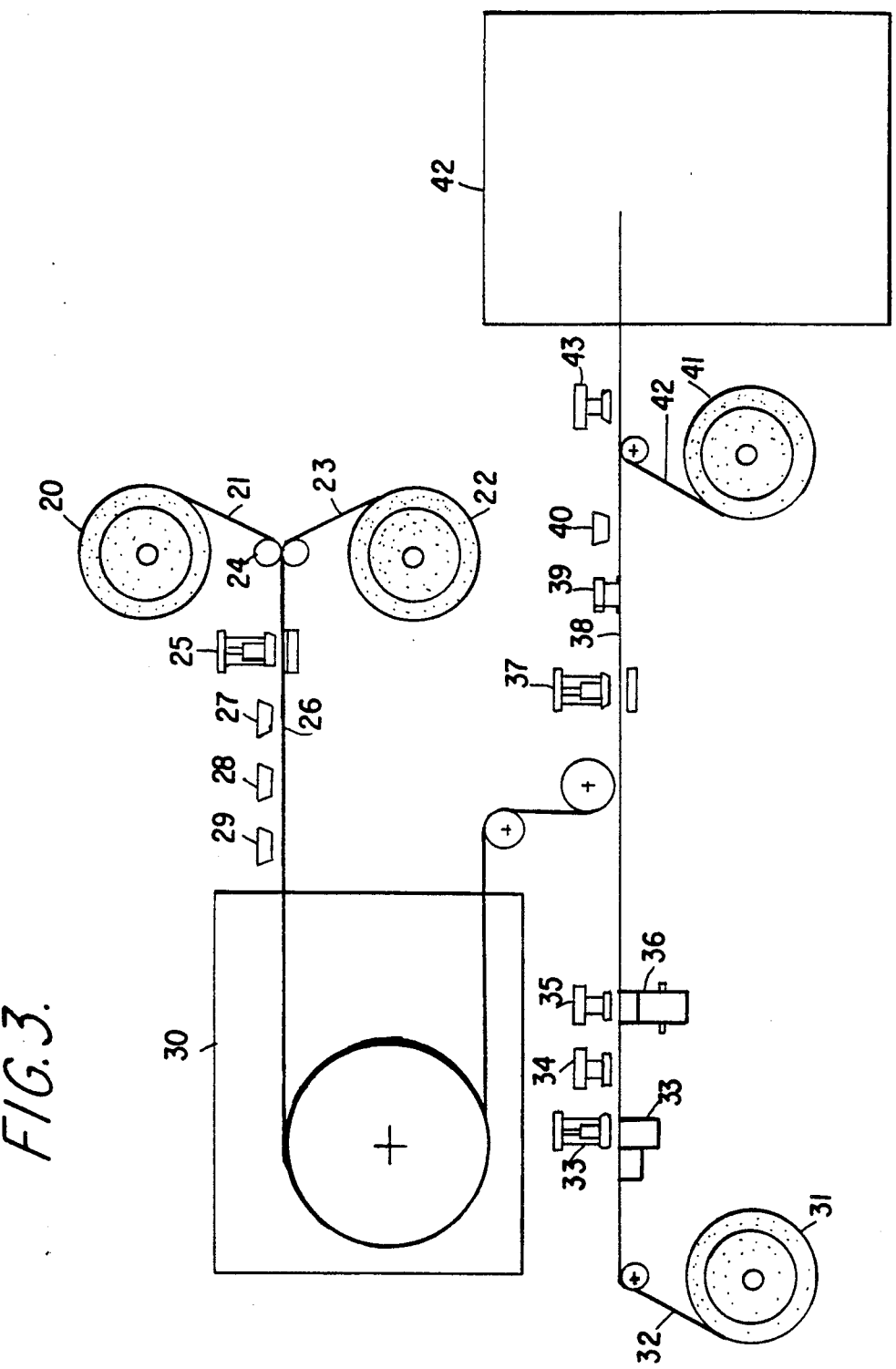
FIG. 3 illustrates a diagram of the procedure for making the device of this invention.

The invention is a self-contained analyzer that quantitatively detects an analyte in a biological fluid. The invention includes a base having a first open reservoir for receiving the biological fluid. A means for separating or partially withholding solids from the biological fluid is provided in the first open reservoir. A channel is provided which draws, by capillary and/or wicking action, the biological fluid from the first open reservoir to a second open reservoir which contains an absorbent. The second open reservoir draws the biological fluid from the channel and, when the second open reservoir is full with the biological fluid, the capillary and/or wicking action terminates. A membrane is provided in the channel which is permeable to the biological fluid. There is at least one chromatic chemical indicator immobilized in the membrane in a predetermined concentration.

The test device or chromatograph of this invention includes a base having at least two compartments which are, desirably, open reservoirs. The first compartment or open reservoir is an opening in the base. The first open reservoir receives a sample of a biological fluid for testing. The first open reservoir has a means for separating solids from the biological fluid. The device of this invention is useful for testing biological fluids that either have or do not have suspended solid matter. The presence of a means for separating or partially withholding solids ensures that only a liquid being tested is exposed to the channel of the device. In this manner cells and other suspended solids are prevented from proceeding further by fiber glass paper, porous plastic, glass beads, and semi-permeable membranes. Numerous varieties of these materials are commercially available.

The device of this invention has a channel that is connected to the first compartment or open reservoir. The biological fluid that is deposited into the first open reservoir is drawn into the channel by capillary and/or wicking action. The drawing of the biological fluid into the channel can be assisted by wicking in the channel. The term "drawing action" for purposes of this invention includes all flow of the biological fluid into and through the channel regardless of whether or not the flow is produced by capillary action alone, by wicking action alone, or by capillary action that is assisted by wicking.

The channel of the device of this invention contains or encloses at least one reagent for detecting the presence of a selected analyte in the biological fluid. The reagent used in this invention can be a combination of compounds and/or enzymes that react simultaneously or sequentially with the selected analyte to produce a detectable reaction product. Desirably, the detectable reaction product produces a color change that is visible to the naked eye. Numerous reagents for detecting the presence of an analyte in a biological fluid are known in the art and are commercially available. These reagents must be immobilized either on the wall of the channel or in a material that is, desirably, stationary within the channel. When more than one reagent is required to detect an analyte, the reagents are, desirably, immobilized in their reaction sequence within the channel or within the first open reservoir and the channel. The reagent that produces the detectable or chromatic reaction product must be present in a calibrated or predetermined concentration within the channel. The term "chromatic chemical indicator" is used in the description of this invention to include the reagent or combination of reagents necessary to detect a selected analyte in a biological fluid. The term "predetermined concentration" is used in the description of this invention to include a concentration of one or more chromatic chemical indicators and/or other reagents that is necessary, in accordance with the art, to produce the reaction results desired for a particular test.

The preferred embodiment of this invention has a material that is, desirably, stationary within the channel. This material is, desirably but not exclusively, a natural or synthetic membrane. Suitable membranes for use in this invention are capable of receiving and immobilizing the selected chromatic chemical indicator and are chemically compatible with the selected chromatic chemical indicator. Suitable membranes are commercially available and can be porous or fibrous materials including filter paper or nylon cloth. The membrane is desirably an integral part of the channel, such as the bottom of the channel, and is sealed in place.

The preferred embodiment of the invention has at least two zones on the membrane within the channel. An initial reaction zone provides reagents to mix and react with an analyte without color formation to form an intermediate compound. A chromatic reaction zone provides reagents to mix and react with the intermediate compound to cause color formation. Many combinations of multiple zone reactions, with or without the formation of intermediate compounds, can be provided with this invention.

The device of this invention has a means for metering the volume of biological fluid that passes through the channel. The means for metering the biological fluid is, desirably, a "pull" compartment or a second open reservoir filled with an absorbent. The geometry, physical nature, and method of incorporation of this pull compartment and the channel can be configured to precisely meter the volume and rate of flow of the biological fluid through the channel. The pull compartment can contain absorbent or porous. materials such as filter paper or porous plastic materials to further control the volume and/or rate of flow of biological material through the channel.

The means for metering the flow of biological fluid through the channel can encompass numerous geometric configurations and/or combinations of materials. The void volume of the pull chamber is the most critical parameter of the means for metering the flow of biological fluid. The density and composition of the material or membrane in the channel as well as the density and composition of any material, optionally, present in the pull compartment can be another parameter effecting the means for metering the flow of biological fluid. For example, the hydrophilic character of these materials or of a thermoformed moisture barrier used to manufacture the upper surface of the device significantly affects the flow of a biological fluid through the device. The pull chamber, in the preferred embodiment of the invention, contains an absorbent of precise volume and precise void volume. The pull chamber draws a precisely metered amount of liquid through the channel. The pull chamber provides a self-metering feature for the device. Regardless of the materials or geometric configuration chosen, it is critical that effective or complete interaction of the analyte in the biological fluid or a derivative thereof occurs with the chromatic chemical indicator. The means for metering the flow of a biological fluid in this invention provides a quantitative assay result in at least 10 minutes and, desirably, in at least 3 minutes.

The dimension of the device of this invention can vary with the intended use. Factors that can vary the dimensions of the device include the amount or nature of chromatic chemical indicator necessary to perform a desired test for a concentration of analyte in a sample of biological fluid to be tested. The dimensions of the device can be selected to control the reaction time of analyte and chromatic chemical indicator and to control the time required to complete the test. The device is desirably between about 70 millimeters and about 200 millimeters long, between about 20 millimeters and about 30 millimeters wide, and between about 3 millimeters and about 15 millimeters high. The opening, through which the sample of biological fluid is placed into the first open reservoir, is desirably between about 3 millimeters and about 15 millimeters. The first open reservoir is desirably between about 6 millimeters and about 35 millimeters in total length, including the opening to the first open reservoir, and between about 8 millimeters and about 15 millimeters in width. The channel is desirably a length sufficient to permit the analyte and chromatic chemical indicator to interact and perform the desired analytical test. The dimensions are desirably sufficient to permit capillary action of the biological fluid. A channel that permits capillary action to occur is desirably between about 50 millimeters and 150 millimeters in length and between about 2 millimeters and about 6 millimeters in width. The second open reservoir is between about 10 millimeters and about 30 millimeters in length and about the same width as the first open reservoir.

The method of this invention uses the device described above. This method is for quantifying analytes in a biological fluid. The method involves receiving a sample of a biological fluid in the first open reservoir. Measurement of the sample is not required before the sample is deposited in the first open reservoir. The quantity of biological fluid received in the first open reservoir must be sufficient to fill the channel and pull compartment.

The biological fluid is filtered as it is received in the first open reservoir by the means for separating solids. The filtered biological fluid is drawn through the channel by capillary and/or wicking action toward the pull compartment. The biological fluid, in the preferred embodiment of the invention, permeates a membrane in the channel. The selected analyte in the biological fluid reacts with the chromatic chemical indicator that is immobilized in the membrane at all expected concentration levels. The point in the channel between reacted analyte and unreacted chromatic chemical indicator traverses the channel as more analyte in the biological fluids is drawn through the channel. When the pull chamber or other means for metering the volume and flow of biological fluid through the channel terminates the flow of biological fluid, the point between reacted and unreacted chemical indicator can be referenced to a concentration of the selected analyte in the biological fluid.

FIGS. 1 and 2, respectively, provide a top plan view and a side plan view of the preferred embodiment of the device of this invention. The device illustrated in FIGS. 1 and 2 is a self-contained quantitative test device 1. The quantitative test device 1 includes a first open reservoir 2 containing a means for separating suspended solids 3 from a biological fluid. The means for separating solids 3 is a porous material such as fiberglass paper, porous plastic or other material having an appropriate mesh and which allows the sample to pass rapidly. The means for separating solids can also include chemical additives to assist in retarding the movement of the suspended matter. The means for separating solids 3 must prevent the majority of solids, such as red cells, from leaving the first open reservoir 2. The liquid phase of the filtered biological fluid is drawn by a membrane 4 through an initial reaction zone 5. The membrane 4a of initial reaction zone 5 can be porous material into which reagents required for a first reaction step have been incorporated. The incorporation of these reagents can be performed by a variety of physical or chemical processes. These processes can include saturating the porous material with a liquid reagent solution followed by drying, or by forming the porous material by coating particles of an insoluble material with the reagents and subsequently using a mass of the coated particles as a porous matrix. Additionally, the porous material can be formed by covalently bonding the chemicals or biologicals of interest to a chemically activated porous matrix.

The channel 6 leads from the first open reservoir 2 which in this embodiment includes the initial reaction zone 5. The channel 6 contains the membrane 4 discussed above. The membrane 4 can be of the same or different material as the membrane 4a used in the initial reaction zone 5. The channel 6 containing membrane 4b forms a chromatic reaction zone 7 wherein the point between reacted and unreacted chromatic chemical indicator (not shown) corresponds to a concentration of analyte in the biological fluid. FIG. 2 illustrates a sample of a scale along the channel 6 which corresponds the point between reacted and unreacted chromatic chemical indicator to a concentration of analyte in the biological fluid.

The chromatic reaction zone 7 of the quantitative test device 1 contains the membrane 4b. Membrane 4b can be a fiber, a membrane strip, or another elongated body containing a predetermined, precise amount of immobilized dye or chromatic chemical indicator. This dye changes color upon either direct interaction with the analyte of interest or indirect interaction with a derivative thereof that is generated or added in the initial reaction zone 5. The relative volume of filtered biological liquid which is contained in the channel 6 is small when compared to the volumes of biological fluid in the first open reservoirs 2 or the second open reservoir 8.

The second open reservoir 8 of this embodiment of the invention provides a means for metering the flow and volume of biological fluid through the channel 6. The second open reservoir 8 of this embodiment of the invention contains a membrane 4c. The membrane 4c is a porous material with high absorptive activity and the ability to rapidly absorb and contain a precise volume of biological liquid. The membrane 4c can be an extension of the membrane 4b or can be another material. The second open reservoir 8 must be partly visible to the user and, desirably, changes color when it is completely saturated with liquid. This provides an optional, but very desirable, third reaction zone 9. When sufficient biological fluid enters the first open reservoir 2, it eventually fills the second open reservoir through capillary and/or wicking action. This condition indicates that the capillary and/or wicking action is terminated and the test results are to be read. Membranes can contain reagents to stabilize the reactants or to reduce interferences with reading the optical scale.

FIG. 3 illustrates the preferred manufacturing equipment for producing the device of this invention. A membrane roll stock 20 feeds a sheet of membrane 21 and a polyethylene laminate roll stock 22 feeds a sheet of polyethylene laminate 23, which forms the base of the device of this invention, into a roller means 24. The membrane 21 and the polyethylene laminate 23 are sealed together by a first heat seal means 25 and form a laminated membrane 26. The laminated membrane 26 passes through at least one liquid dispensing means. The liquid dispensing means in the preferred embodiment of the equipment is a plurality of liquid dispensers 27, 28, and 29. The liquid dispensers 27, 28, and 29 selectively spray dye, enzymes, or another chromatic chemical indicator onto the membrane portion of the laminated membrane 26. The sprayed laminated membrane 26 is then dried in a drying chamber 30.

A clear PVC roll stock 31 feeds sheet PVC 32 through a thermoform means 33, two hole punch means, and a draw zone and filter insert means 36. The filter-inserted PVC 32 is laminated with the laminated membrane 26 in a second heat seal means 37. The membrane 21 is enclosed between the polyethylene laminate 23 and the PVC 32 upon existing the second heat seal means 37 and forms an enclosed membrane 38. The enclosed membrane 38 passes through printer means 39 and 40 where a scale is printed onto the enclosed membrane 38 next to the channel 6 of FIG. 2.

A foil roll stock 41 feeds a foil 42 to the PVC 32 side of the enclosed membrane 38. The foil 42 provides a peelable, protective packaging for the device of this invention. Individual devices are cut from one another in a cutting station 43. The individual devices are then conveyed to an automated boxing machine 42. An electronic monitoring means (not shown) is desirably provided to regulate, via appropriate continuous feedback control means, the operation of the various elements of the manufacturing equipment.

The device and method of this invention can be used for a number of different assays. These assays can include assays wherein the analyte of interest is converted to a reactive compound that is able to produce or destroy a dye. Additionally, these assays can include assays wherein the analyte of interest competes with a labelled derivative of itself for a limited number of binding sites supplied by a specific binder embedded in the membrane in the channel. The specific binder can be an antibody, an antigen, or a receptor molecule. After binding occurs, the labelled derivative is visualized in the detection zone of the channel by a reaction specific to the label. This can be an enzymatic reaction leading to a visible color change or the label itself can be visible in the device. Labels can include particles, liposomes loaded with dyes, and dyes themselves.

The device and method of this invention can be used for a large number of specific assays. The assays can involve the two general categories of assays discussed above which are chemical reaction assays and reactions involving "binder" assays. Examples of chemical reaction assays include test for cholesterol, HDL cholesterol, triglycerides, glucose, uric acid and potassium. Examples of "binder" reaction assays involving antibodies, antigens, or receptors include (1) tests for viruses such as AIDS, rubella, and herpes, (2) tests for hormones to determine pregnancy and thyroid status, and (3) tests for drugs such as tests for digoxin, phenobarbital, and theophylline, and others.

The following examples are provided as specific embodiments of the invention and are not intended to limit either the device or method of this invention.

EXAMPLES

These examples are specific descriptions of the invention. Example 1 represents the preferred embodiment of the device and method of this invention. This example analyzes cholesterol in whole blood. Examples 1 and 2 use the following materials.

Materials Used for Manufacturing the Device

The membrane used to manufacture the device of this example is an "activated" membrane. Activated membranes have reactive chemical groups which react with amino and carboxyl groups of proteins, antibodies and dyes in order to form covalent bonds. Commercial sources for a suitable membrane materials include those sold by Millipore Intertech, Bedford, Mass. 01730. The membranes are called Immobilon-AV Affinity Membranes. These membranes consist of chemically derivatized hydrophilic polyvinylidene fluoride. Alternative membranes are provided by the Pall Biosupport Corporation, Subsidiary of Pall Corporation, 77 Crescent Beach Road, Glen Cove, N.Y. 11542. These membranes are called Immunodyne Membranes and consist of chemically modified Nylon 66. Gelman Sciences, Inc., 600 South Wagner Road, Ann Arbor, Mich. 48106 provides membranes called UltraBind Membranes. The chemical composition of these membranes is not available. Immunodyne membranes by Pall Biosupport Corporation were used for this example.

The top moisture barrier of the device consists of clear 0.015 inch thick PVC roll stock. The bottom base is the same material and can also be manufactured from SARAN enforced PVC or a polyethylene laminate. A removable peel-off protective strip, covering the upper surface of the device is desirably provided and consists of polyethylene-laminated aluminum foil.

EXAMPLE 1

Example 1 provides an quantitative determination of cholesterol in whole blood. This example represents the preferred embodiment of the invention. The materials and device described above are used in this example.

PREPARATION OF INDIVIDUAL TEST DEVICES

Reagent 1

The following enzyme reagent was prepared for application to the membrane in the channel.

TABLE 1

|  | General Range | Preferred Composition | Approximate per strip area (meter$^2$) |
|---|---|---|---|
| cholesterol esterase | 100–1500 U | 600 U | 6000 U |
| cholesterol oxidase | 100–1500 | 400 U | 4000 U |
| sodium cholate | 1–50 mg | 10 mg | 100 mg |
| ascorbic acid oxidase | 10–500 U | 100 U | 1000 U |
| triton X100 | 1–100 l | 10 l | 100 l |
| potassium hydrogen phosphate |  | 0.3 g | 0.3 g |
| disodium hydrogen phosphate dihydrate |  | 0.85 g | 8.5 g |
| deionized water | 10 ml | 10 ml |  |

Reagent 2

The following dye reagents were prepared for application to the channel. The reagent of Table 2a was used in this example.

TABLE 2a

|  | General Range | Preferred Composition | Approximate amount per strip area (meter$^2$) |
|---|---|---|---|
| 4Cl-1-naphthol | 0.2–200 mg | 50 mg | 500 mg |
| methanol or | 10 ml | 10 ml |  |

TABLE 2b

|  | General Range | Preferred Composition | Approximate amount per strip area (meter$^2$) |
|---|---|---|---|
| docetyl sodium sulphosuccinate | 1–20 mg | 10 mg | 100 mg |
| 3, 3', 5, 5'-tetra-methyl-benzidine | 0.2–100 mg | 10 mg | 100 mg |
| acetone | 10 ml | 10 ml |  |

Reagent 3

TABLE 3

|  | General Range | Preferred Composition | Approximate per strip area (meter$^2$) |
|---|---|---|---|
| peroxidase | 1000–50,000 U | 10,000 U | 100,000 U |
| potassium dihydrogen phosphate |  | 0.03 g | 0.03 g |
| disodium hydrogen phosphate dihydrate |  | 0.85 g | 8.5 g |
| polyvinyl pyrolidone or triton X100 |  | 0.05 ml | 0.5 ml |

Reagent 3 is a peroxidase reagent for the channel.

Manufacture of the Device

FIG. 3 provides a flow diagram of the preferred manufacturing equipment to assemble the device of this example.

Membrane 21 and polyethylene laminate 23 pass through the first heat seal means 25 in order to form the bottom section of the device. In the first jet ink dispenser 27, 10 microliters of enzyme reagent are delivered into the initial reaction zone and 10 microliters of dye solution reagent 2 are dispensed evenly by the second jet ink dispenser 28 into the detection channel. The third jet ink dispenser 29 sprays 10 microliters of peroxidase solution reagent 3 are delivered into the detection section of the channel. The reagents are dried and then sealed into the device.

Procedure

Whole blood, obtained from a finger prick is transferred into the first open reservoir of the device of FIG. 1. The means for separating solids retains the bulk of the red cells. Cell free or cell poor plasma enters the initial reaction zone which contains the enzymes cholesterol esterase and cholesterol oxidase and certain salts and solubilizers such as surfactants. The initial reaction zone also contains the enzyme horseradish peroxidase. Plasma cholesterol is converted to cholestanone and hydrogen peroxide in the initial reaction zone.

The plasma containing these reaction products and the other reagents dissolved in the initial reaction zone enter the channel, which contains a precise amount of a dye immobilized on a physical matrix which is a membrane. In the presence of horseradish peroxidases, the dye is quantitatively oxidized by hydrogen peroxide and converted into a colored species. The dye is evenly distributed in the compartment and its conversion occurs immediately upon contact with hydrogen peroxide. Therefore, the length of the color converted area is proportional to the amount of hydrogen peroxide, and, therefore, to the amount of cholesterol in the sample.

Plasma, devoid of hydrogen peroxide, enters the pull chamber. While the pull chamber is being filled, the oxidation of the dye in the channel continues until the pull chamber is completely filled, at which time the process stops. The length of the color bar formed in the channel is read from a scale which has been calibrated in cholesterol concentration units.

EXAMPLE 2

Example 2 provides a quantitative analysis of theophylline in whole blood. The materials and procedures are the same as those described for Example 1 except as follows.

PREPARATION OF INDIVIDUAL TEST DEVICES

Reagent 4

The following theophylline-horseradish peroxidase conjugate reagent was prepared.

TABLE 4

|  | General Range | Preferred Composition | Approximate amount per strip area ($m^2$) |
|---|---|---|---|
| theophylline peroxidase conjugate | .5–5 micromole | 1 micromole | 10 micromoles |
| triton X100 | 1–100 microml | 10 micromole | 100 micromoles |
| potassium hydrogen phosphate |  | 0.03 g | 0.3 g |
| disodium hydrogen phosphate dihydrate |  | 0.85 g | 8.5 g |
| deionized water | 10 ml | 10 ml |  |

Reagent 5

The following anti-theophylline antibody solution was prepared.

| anti-theophylline antibody | 5–50 micromole | 10 micromole | 100 micromole |
|---|---|---|---|
| triton X 100 | 1–100 micromole | 10 micromole | 100 micromole |
| potassium hydrogen phosphate |  | 0.03 g | 0.3 g |
| disodium hydrogen phosphate dihydrate |  | 0.85 g | 8.5 g |
| deionized water | 10 ml | 10 ml |  |

Reagent 3

A dye solution, as described above under "cholesterol reagent", was prepared.

4. urea peroxide, powder

Manufacture of the Device

FIG. 3 provides a flow diagram of the preferred manufacturing equipment to assemble the device of this example.

Membrane 21 and polyethylene laminate 23 pass through the first heat seal means 25 in order to form the bottom section of the device. In the first jet ink dispenser 27, 10 microliters of antibody solution are dispensed evenly into the detection channel and 20 microliter of 1/10 molar ammoniumchloride solution are delivered into the initial reaction zone by the second jet ink dispenser in order to neutralize the binding sites of the membrane in that section of the device. Additional jet ink dispensers spray 10 microliters of dye solution into the detection section and 10 microliters of theophylline-horseradish peroxidase conjugate solution into the initial reaction zone of the device. These reagents are dried and then sealed into the device.

In the lower mechanism of the manufacturing equipment, the clear PVC roll stock is thermoformed and filters for the first open reservoir and the pull chamber are inserted. After insertion of the filters, 5 milligram of urea peroxide are added on top of the blood separation filter of compartment 1 and subsequently sealed into the device.

Procedure

Whole blood enters the first open reservoir as previously described. Blood cells are retained in this compartment and plasma moves via wicking action into the initial reaction zone. The initial reaction zone contains a conjugate of theophylline and horseradish peroxidase in predetermined, precise quantities. When cell free poor plasma enters compartment 2, a precise volume of plasma completely takes up the theophylline conjugate and a homogeneous solution of the theophylline conjugate in plasma is generated.

A precisely measured aliquot of the plasma leaving the first open chamber is homogeneously mixed with a precise amount of drug derivative. The drug derivative is distributed in the initial reaction zone in the form of a thin film covering the exterior and interior surfaces of the porous material which constitutes the zone. The initial reaction zone is designed such that plasma is capable of entering it very rapidly without immediately entering the analytical compartment. The first open reservoir and the initial reaction zone also contain chemical additives which release plasma protein bound theophylline.

The homogeneous mixture moves into the channel which contains a precise amount of antibody against theophylline. The antibody is evenly distributed over the compartment and immobilized on it along with a dye that is oxidizable by peroxide in the presence of horseradish peroxidase. A dry hydrogen peroxide such as urea peroxide is also embedded in the membrane of the channel. The antibody against theophylline also reacts with the theophylline horseradish peroxidase conjugate.

When theophylline is absent from the plasma, the theophylline conjugate is taken up by the antibody. In the very first section of the channel. However, in the presence of theophylline, which competes with the conjugate for the limited number of antibody sites on the solid matrix in the channel, some of the antibody sites in channel are being blocked by plasma theophylline. With increasing concentration of theophylline in the plasma, the last unbound conjugate molecule has to travel farther and an increasing distance through the channel in order to find an immobilized binding partner. The fraction of the channel traversed to find an immobilized conjugate, therefore, becomes longer with increasing concentration of theophylline in the plasma.

The theophylline horseradish peroxidase conjugate color converts the immobilized dye in the channel through oxidation with peroxide along its migration path. This process stops after the last conjugate molecule becomes immobilized. The results of this process shows a color bar whose length is proportional to the concentration of drug in the whole blood sample.

The pull compartment provides the same "pull" effect like in the previous example and furnishes evidence that the test is complete.

EXAMPLES 3 AND 4

Examples 3 and 4 provide, respectively, the reagents necessary to manufacture devices for quantitatively analyzing in whole blood glucose and triglycerides. The procedures for manufacturing the devices of these examples are the same as described in Example 1. Tables 6 and 7 provide the reagents and their concentrations for these examples.

TABLE 6

Device for Analyzing Glucose

| | Generic Range | Preferred Composition | Conc./Area (Units/m$^2$) |
|---|---|---|---|
| Glucose Oxidase | 100–10,000 U | 1000 U | 10,000 U |
| Potassium Dihydrogen Phosphate | | 0.03 g | 0.3 g |
| Disodium Hydrogen Phosphate Dihydrate | | 0.85 g | 8.5 g |
| Deionized Water | | 10 ml | |

TABLE 7

Device for Analyzing Triglycerides

| | | | |
|---|---|---|---|
| Glycerol Kinase | 100–10,000 U | 2,000 U | 20,000 U |
| Lipase | 500–100,000 U | 10,000 U | 100,000 U |
| Glycerol Phosphate Oxidase | 100–50,000 U | 12,000 U | 120,000 U |
| ATP | | 40 uMOLE | 0.4 mMOLE |
| Triton X100 | | 20 uL | 200 uL |
| Magnesium Sulfate | | 20 uMOLE | 0.2 mMOLE |
| Sodium Chloride | | 200 uMOLE | 2 mMOLE |
| Pipes Buffer | | 50 uMOLE | 0.5 mMOLE |
| Deionized Water | | 10 mL | |

The devices of Examples 3 and 4 are used in the same manner as is the device of Example 1.

I claim:

1. A method for quantitatively analyzing a biological fluid for an analyte comprising the following steps:
    depositing a biological fluid sample in a first open reservoir of an analytical device, said first open reservoir having means for separating solids from a fluid sample, whereby solids in said biological fluid sample are substantially retained in said first open reservoir;
    drawing said biological fluid sample through a channel from said first open reservoir to a second open reservoir to fill said second open reservoir with said biological fluid sample, said second reservoir being configured so as to draw a precise predetermined volume of biological fluid sample through said channel;
    said channel including a permeable membrane having at least one reagent specific for the analyte to be determined, said reagent including a chromatic indicator immobilized in said membrane in a predetermined amount to quantify the analyte in said biological fluid, whereby analyte in said biological fluid sample reacts with said reagent to produce a color change in said channel;
    said channel being provided with calibration means related to said color change to quantify the amount of analyte present in said biological fluid sample.

2. The method according to claim 1 wherein said reagent is selected form the group consisting of enzymes, labeled antibodies, unlabeled antibodies, antigens, and a dye.

3. The method according to claim 1 wherein said analyte is selected from the group consisting of cholesterol, glucose, HDL cholesterol, triglycerides, hormones, drugs, infectious agents, and antibodies.

4. The method according to claim 2 wherein said chromatic indicator comprises cholesterol esterase, cholesterol oxidase, ascorbic acid oxidase, sodium cholate, a surfactant, peroxidase, 4Cl-1-naphthol, and a buffer.

5. The method according to claim 2 wherein said chromatic indicator comprises cholesterol esterase, cholesterol oxidase, ascorbic acid oxidase, sodium cholate, a surfactant, peroxidase, 3,3',5,5'-tetramethyl benzidine, and a buffer.

6. The method according to claim 2 wherein said chromatic indicator comprises glucose oxidase, peroxidase, 4Cl-1-1 -naphthol and a buffer.

7. The method according to claim 2 wherein said chromatic indicator comprises glucose oxidase, peroxidase, 3,3',5,5'-tetramethyl benzidine, and a buffer.

8. The method according to claim 2 wherein said chromatic indicator comprises glycerol kinase, lipase, glycerol phosphate oxidase, ATP, a surfactant, 4Cl-1-naphthol and a buffer.

9. The method according to claim 2 wherein said chromatic indicator comprises glycerol kinase, lipase, glycerol phosphate oxidase, ATP, a surfactant, 3,3',5,5'-tetramethyl benzidine, and a buffer.

10. The method according to claim 1 wherein said reagent is selected from the group consisting of labeled drugs, labeled hormones, and labeled antibodies.

11. The method according to claim 10 wherein said reagent comprises peroxidase labeled conjugate of theophylline, an antibody against theophylline, urea peroxide, and a buffer.

12. The method according to claim 11 wherein said reagent comprises a labeled antibody, an antigen to the antibody to be analyzed.

13. The method according to claim 11 wherein aid biological fluid sample is whole plasma.

14. In a method for quantitatively analyzing a biological fluid for an analyte by contacting said biological fluid sample with a membrane having immobilized thereon at least one reagent specific for the analyte to be determined, said reagent including a visually observable chromatic indicator, the improvement comprising:

drawing said biological fluid sample from a first open reservoir through a channel including a permeable membrane having a reagent immobilized in said membrane to a second open reservoir wherein said biological fluid sample is substantially completely reacted with the reagent immobilized in the membrane, such that said second reservoir is configured to meter the volume of the biological fluid sample through said channel.

* * * * *